US008965070B2

(12) United States Patent
Bredno

(10) Patent No.: US 8,965,070 B2
(45) Date of Patent: Feb. 24, 2015

(54) INTERACTIVE COMPUTER-AIDED DIAGNOSIS

(75) Inventor: Joerg Bredno, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 1579 days.

(21) Appl. No.: 10/598,309

(22) PCT Filed: Mar. 3, 2005

(86) PCT No.: PCT/IB2005/050783
§ 371 (c)(1), (2), (4) Date: Aug. 12, 2008

(87) PCT Pub. No.: WO2005/086065
PCT Pub. Date: Sep. 15, 2005

(65) Prior Publication Data
US 2008/0294591 A1 Nov. 27, 2008

(30) Foreign Application Priority Data
Mar. 5, 2004 (EP) .................................... 04100895

(51) Int. Cl.
*G06K 9/00* (2006.01)
*G06F 19/00* (2011.01)

(52) U.S. Cl.
CPC ........... *G06F 19/345* (2013.01); *Y10S 707/915* (2013.01)
USPC ........................... 382/128; 382/131; 707/915

(58) Field of Classification Search
CPC .................................................... G06F 19/345
USPC .................................. 707/915; 382/128, 131
See application file for complete search history.

(56) References Cited

U.S. PATENT DOCUMENTS 5,603,322 A * 2/1997 Jesmanowicz et al. ....... 600/410
6,477,399 B2 11/2002 Biswal et al.
6,574,357 B2 6/2003 Wang
2002/0028006 A1* 3/2002 Novak et al. ................. 382/128
2003/0095697 A1 5/2003 Wood et al.
2004/0073105 A1* 4/2004 Hamilton et al. ............ 600/410

FOREIGN PATENT DOCUMENTS

WO WO9612187 A 4/1996
WO WO0174238 A1 10/2001
WO WO0242998 A2 5/2002

OTHER PUBLICATIONS

Poliakov et al., Proc. AMIA Symp., 2001, pp. 533-537.*
Globus A. et al: "14 Ways to Say Nothing With Scientific Visualization"; IEEE Computer 27 (7); pp. 86-88, 1994.A.
Bredno J. et al: "Automatic Parameter Setting for Balloon Models"; Procs. SPIE vol. 3979, 2000; pp. 1185-1195.

(Continued)

*Primary Examiner* — Cheyne D Ly

(57) ABSTRACT

Despite intense research activities in the field of computer-aided diagnosis methods of computer vision, automated classification or comparable algorithmic solutions are not regularly used and even less regularly trusted by physicians. According to an exemplary embodiment of the present invention, a confidence interval of the performed diagnosis is visualized and a standardized feedback mechanism is provided which allows for an interactive improvement of the method.

9 Claims, 4 Drawing Sheets

30 40 32 34 36 38 42 44

(56) References Cited

OTHER PUBLICATIONS

Figure 1:
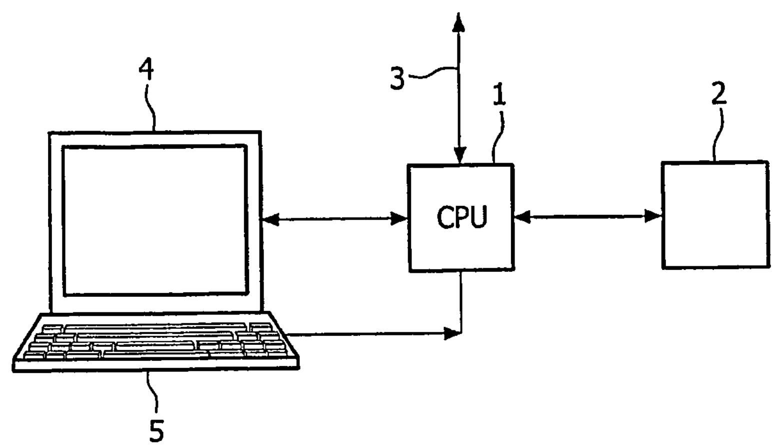

Lehmann T. M. et al: “Texture-Adaptive Active Contour Models”; LCNS 2013, 2001; pp. 387-396.

Nichols, T. “Visualizing Variance With Percent Change Threshold”; Whole Document; Dec. 19, 2002.

* cited by examiner

INTERACTIVE COMPUTER-AIDED DIAGNOSIS

The present invention relates to the field of computer-aided data processing (CADx). In particular, the present invention relates to a method of computer-aided extraction of quantitative information, to a data processing device and to a corresponding computer program for a data processing device.

Despite intense research activities in the field of computer-aided diagnosis, the transfer of resulting algorithms to the target market, i.e. clinical applications, is often not successful. Methods of computer vision, automated classification, or comparable algorithmic solutions are not regularly used and even less regularly trusted by physicians.

The most important reasons for such distrust toward research results include:

field testing in limited environments, data processing methods remain incomprehensible to non-technical users, and dependency of the quality of an algorithm from technical parameter settings.

Despite growing awareness of insufficient validations, inappropriate approaches such as, for example, described by Globus A. et. al. “14 ways to say nothing with scientific visualization” IEEE Computer 27 (7) pp. 86-88, 1994 are used. The computer vision algorithms are mostly validated by subjective visual impression of the researchers themselves. A quantitative confidence standard for all applications of CADx and similar applications is required to increase a well-founded trust of physicians towards these applications.

WO 01/74238 A1 discloses methods of localizing a deviant region in a turbid medium to be used in optical mammography where a breast of a female body is examined by means of light. Said methods produce images in which any deviations, for example tumors, can be recognized.

It is an object of the present invention to provide for an improved computer-aided extraction of quantitative information.

According to the invention, a method of computer-aided extraction of quantitative information, a data processing device and a computer program for a data processing device for performing a computer-aided extraction of quantitative information according to the independent claims are provided.

According to an exemplary embodiment of the present invention, a method of computer-aided diagnosis is provided wherein acquired first diagnostic data is processed on the basis of a first parameter set to determine a first diagnosis result. Then, a confidence interval is determined with respect to the diagnosis result. The first diagnosis result and the confidence interval is displayed, for example, to a user. The first parameter set is then adjusted on the basis of an input, for example, from a user of the system. Then, the diagnostic data is reprocessed on the basis of the adjusted first parameter set to determine a second diagnosis result which is displayed.

According to this exemplary embodiment of the present invention, a multi-step-methodology is suggested which is applicable to a plurality of image- and signal processing algorithms that are often the base of clinical data processing applications. According to an aspect of this exemplary embodiment of the present invention, a confidence interval with respect to the first diagnosis result is provided. In other words, a feedback is provided to the user of the method which gives the user a feeling with respect to the dependability of the diagnosis. For example, for quantitative measurements, a 95% interval (“in 19 of 20 cases, the true result will be in the following range”) may be part of the confined presentation.

Geometric results, such as segmentations or registrations of, for example, organs of a patient may instead of a statistic visualization of the confidence interval be displayed with an explorable “grey area” representing the area where the segmented or registered form may be varying.

By an appropriate input, the user may alter the first parameter set. Then, a reprocessing of the diagnostic data may be performed on the basis of the adjusted first parameter set to determine the second diagnosis result. From this, the user of the system comes to know the influence of the changed parameter on the diagnosis result, and therefore the stability and reliability of the computed result.

Advantageously, due to the confidence feedback, a trust in the system or method may be improved. Furthermore, due to the variation of the parameters, the user may interactively explore the influence of certain parameters or certain parameter ranges on the diagnosis result to thereby establish a feeling with respect to the dependability of the diagnosis result.

According to another exemplary embodiment of the present invention, at least one parameter of the first parameter set may be varied by a user by a corresponding input. This may allow for an interactive reprocessing of the diagnostic data.

According to another exemplary embodiment of the present invention, a distrust selection option is provided, for example, to the user of the system upon selection of which the first diagnostic data and the corresponding first parameter set is forwarded to a service port such that, for example, an R&D team may use this information for further adjusting the method. For example, the selection of the distrust selection option may result in a storage of the data of the actual case in an anonymised data base. A customer advantageously may collect this data and pass it on to marketing and R&D. This may allow that a user feels more empowered to increase the quality of the method. Preferably, the range of parameters is extracted from clinical data acquired at the site of application, which enables each embodiment of the invention to individually adapt to clinical setups.

According to another exemplary embodiment of the present invention, a trust selection option is provided upon selection of which the first parameter set may be stored together with the first diagnostic data. This set of first parameter set and first diagnostic data which has been proved to be appropriate may be used as ground truth for other diagnosis or may, for example, also be used for further training of the method or system.

According to another exemplary embodiment of the present invention, the first diagnostic data may be compared to second diagnostic data. A similarity of the first and second diagnostic data may be determined and when the similarity meets with that criteria, the first diagnostic data may be reprocessed on the basis of a second parameter set originally belonging to the second diagnostic data.

According to another exemplary embodiment of the present invention, the methods allow for an explorative determination of a dependability of at least one of three first and second diagnosis results.

According to another exemplary embodiment of the present invention, a data processing device is provided allowing for a visualization of a confidence interval relating to a diagnosis performed on the basis of a parameter sets. Furthermore, this data processing device may allow for a reprocessing of the diagnostic data on the basis of an adjusted parameter set. This reprocessing may have the following effects.

As a first effect, by adjusting the first parameter set, a second diagnosis result may be achieved which is more accurate. As a second effect, by adjusting the parameters of the first parameter set, a user may explore the dependability of the diagnosis result from the parameters. By this, the confidence interval may be visualized.

The present invention relates also to a computer program for a data processing device for performing a computer-aided diagnosis. The computer program according to the present invention is preferably loaded into a working memory of a data processor. The data processor is thus equipped to carry out the method of the present invention. The computer program may be stored on a computer readable medium, such as a CD-ROM. The computer program may also be presented over a network, such as the WorldWideWeb and can be downloaded into the working memory of a data processor from such a network. The computer program may be written in any suitable programming language, such as C++.

It may be seen as the gist of an exemplary embodiment of the present invention that a confidence interval relating to the dependability of the diagnosis result on certain parameters is visualized. On the basis of an input, the diagnostic data may be reprocessed on the basis of an adjusted parameter set to determine a second diagnosis result which is displayed on the display. Furthermore, standardized feedback mechanisms, such as trust or distrust selection options may be provided allowing users to express their individual trust with respect to the method and/or system and to furthermore improve presented results by allowing that this feedback may automatically be used for further improving the method or system.

Exemplary technical fields, in which the present invention may be applied, include baggage inspection, medical applications, material testing, and material science. Even in the case of medical applications, it is not necessary that the various methods steps have to be carried out by a physician.

These and other aspects of the present invention are apparent from and will be elucidated with reference to the embodiment described hereinafter and with respect to the following drawings:

FIG. 1 shows a schematic representation of a data processing device according to an exemplary embodiment of the present invention which is adapted to execute a method according to an exemplary embodiment of the present invention.

Figure 2A:
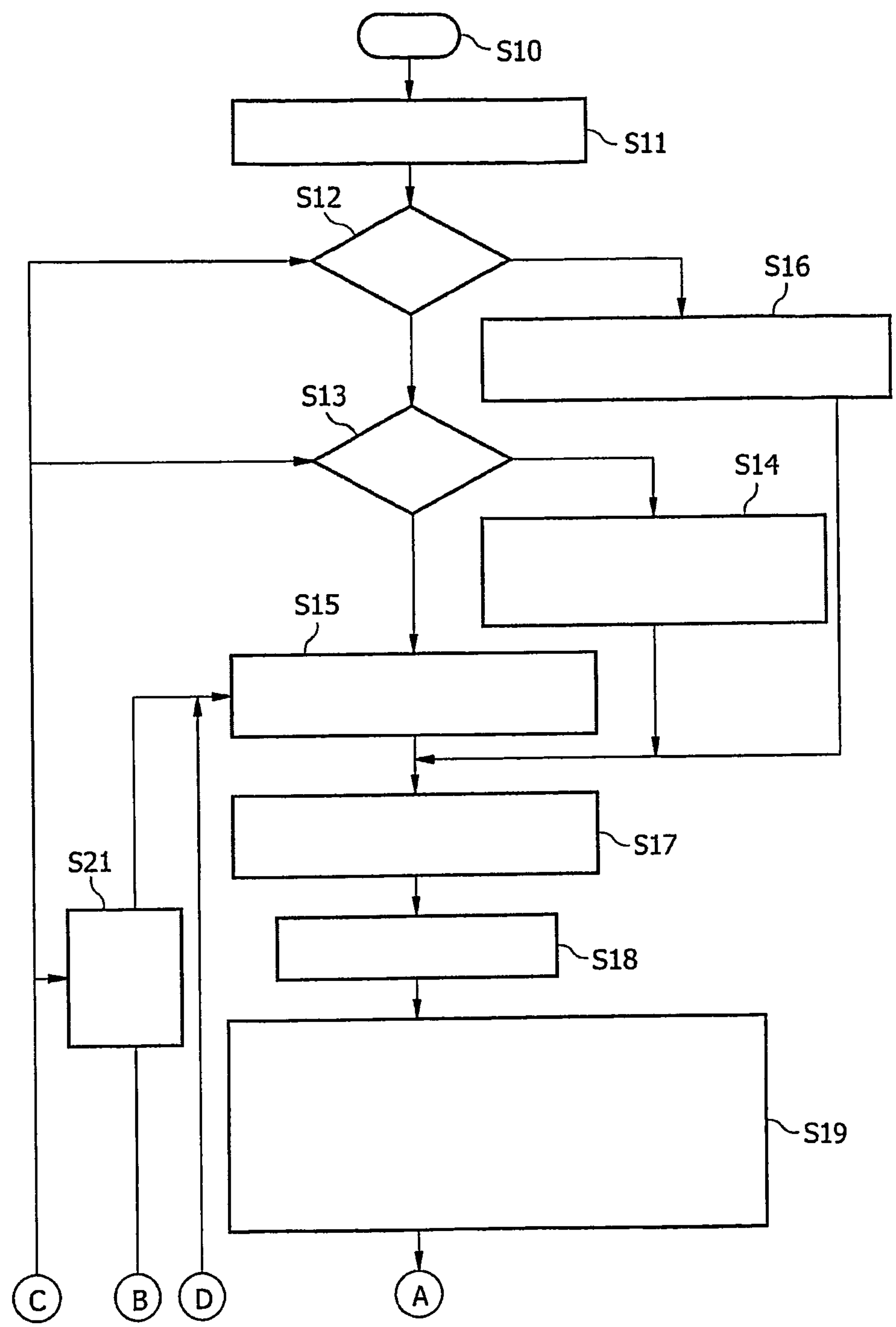

FIGS. 2*a* and *b* show a flowchart of an exemplary embodiment of a method of operating the data processing device of FIG. 1 according to an exemplary embodiment of the present invention.

Figure 3:
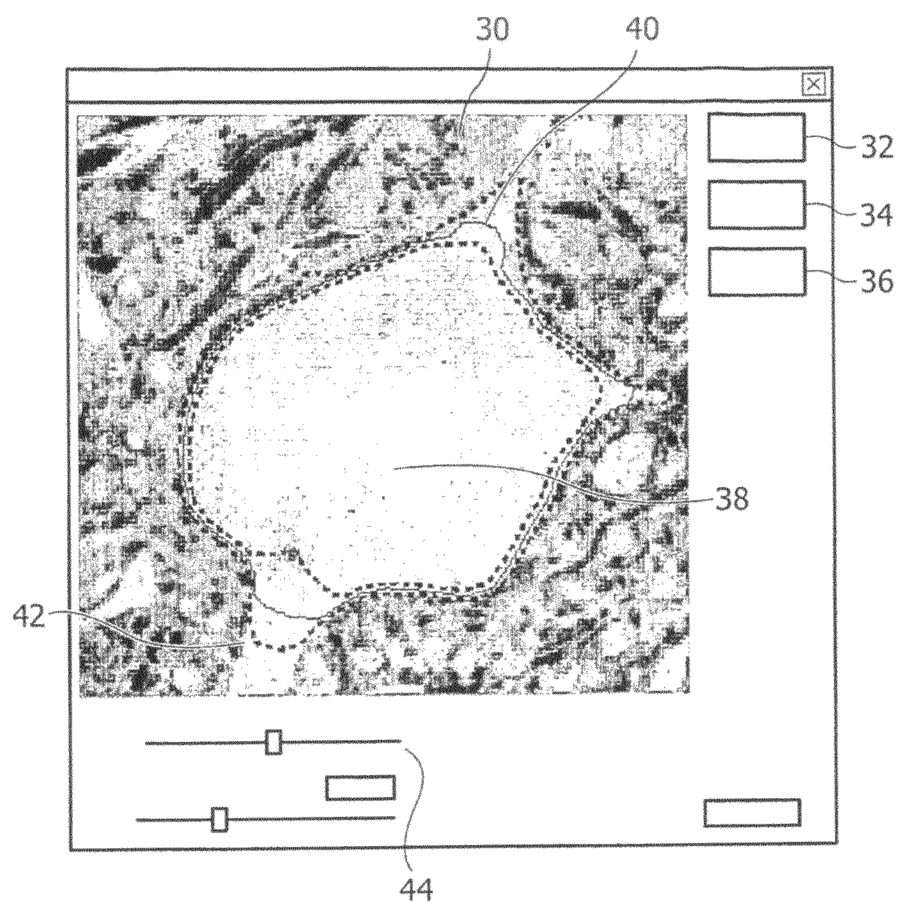

FIG. 3 shows an exemplary embodiment of a display presented to a user according to the present invention.

FIG. 1 depicts an exemplary embodiment of a data processing device according to the present invention for executing an exemplary embodiment of a method in accordance with the present invention. The data processing device depicted in FIG. 1 comprises a central processing unit (CPU) or data processor 1 connected to a memory 2 for storing the diagnostic data, the parameter sets or any intermediate results. The data processor 1 may be connected to a plurality of input/output-, network- or diagnosis devices, such as MRI devices or CT devices via one or more data transfer mechanisms. The image processor is furthermore connected to a display device 4 (e.g. a computer monitor) for displaying information or images computed or adapted by the data processor 1. An operator or user may interact with the data processor 1 via a keyboard 5 and/or other output devices which are not depicted in FIG. 1.

FIGS. 2*a* and *b* show a flow-chart of an exemplary embodiment of a method for performing a computer-aided diagnosis in accordance with the present invention.

The following exemplary embodiment relates to the field of computer-aided viewing. However, it should be noted that the present invention may be applied to a variety of application fields, such as, for example, computer assisted navigation in surgery, intervention planning, outcome control or others.

After the start in step S10 the method continues to step S11 where diagnostic image data is acquired. The diagnostic image data may, for example, be an image from a microscope. Then, the method continues to step S12 where a determination is made with respect to whether there is a ground truth for this diagnostic image data or not. In case it is determined in S12 that there is ground truth for this diagnostic image data, the method continues to step S16 where a first parameter set is set corresponding to third parameters of the ground truth. Then, the method continues to step S17.

The adjusted parameters of the parameter sets may comprise a significance level for statistical tests, thresholds for binary decisions, weighting factors for the combination of different processing steps, and scales and coefficients of image filters. In a further embodiment, additionally properties of the input image data like intensity, contrast, and noise intensity can be changed so that the stability of computed results to these image properties can be displayed to the user as well.

In case it is determined in step S12 that there is no ground truth, the method continues to step S13 where it is determined whether there is comparable data stored in a memory or not. In case it is determined that there is comparable data in an accessible memory, the method continues to step S14 where the first parameter set is set in accordance to second parameters that were valid for the comparable data. Then, the method continues to step S17.

In case it is determined in step S13 that there is no comparable data, the method continues to step S15 where the first parameter set is set in accordance with a preset parameter range. Then, the method continues to step S17.

In step S17 a computer-aided diagnosis is performed on the basis of the first parameter range. Then, the method continues to step S18 where the diagnosis result is displayed to a user of the system, for example on display 4. Then, the method continues to step S19 where a dependability or trustworthiness of the displayed diagnosis result may be explored by a user by adjusting variables of the first parameter set. The adjusted variables are used to reprocess or re-perform a diagnosis to determine new diagnosis result. The new or adjusted diagnosis result is then displayed to the user, for example via display 4.

The user may, for example, adjust variables by moving a slider by means of a pointing device, such as a mouse pointer on a display. Also, for example, a track ball, mouse or mouse wheel may be used to adjust the variables.

Advantageously, by adjusting the parameters, the user may explore the dependability or trust worthiness of the diagnosis result. In particular, the dependability of the diagnosis result may be explored with respect to the adjusted variables. In other words, by exploring the dependability or trust worthiness, a quantitative confidence measurement may be conveyed to the user of the system.

In a variant of this exemplary embodiment of the present invention, is also possible to provide quantitative confidence. For example, the methods may include visual feedback on the result probability distribution due to algorithmic uncertainties. For example, for quantitative measurements, a 95% interval ("in 19 of 20 cases, the true result will be in the following range") may be part of the confined presentation to the user on display 4. Geometric uncertainties with respect to geometric results obtained, for example, by a segmentation or registration may advantageously be not statistically visualized by using numbers but with an explorable "grey area", such as, for example, depicted in FIG. 3.

During the development and the initial configuration of the method, not only a set of technical parameters is determined which delivers in the middle the best result but for all available training data an individual parameter set is determined which reproduces a known gold truth in a most appropriate manner. From this, for each parameter, a variance range may be provided or displayed to the user. Then, as described above, the user may use an input means, such as a mouse, mouse wheel or a windows slider displayed on the display to adjust a parameter within this variance range. Advantageously, according to this aspect of the present invention, the user may directly (interactively) follow the changes to the diagnosis result on the display.

Figure 2B:
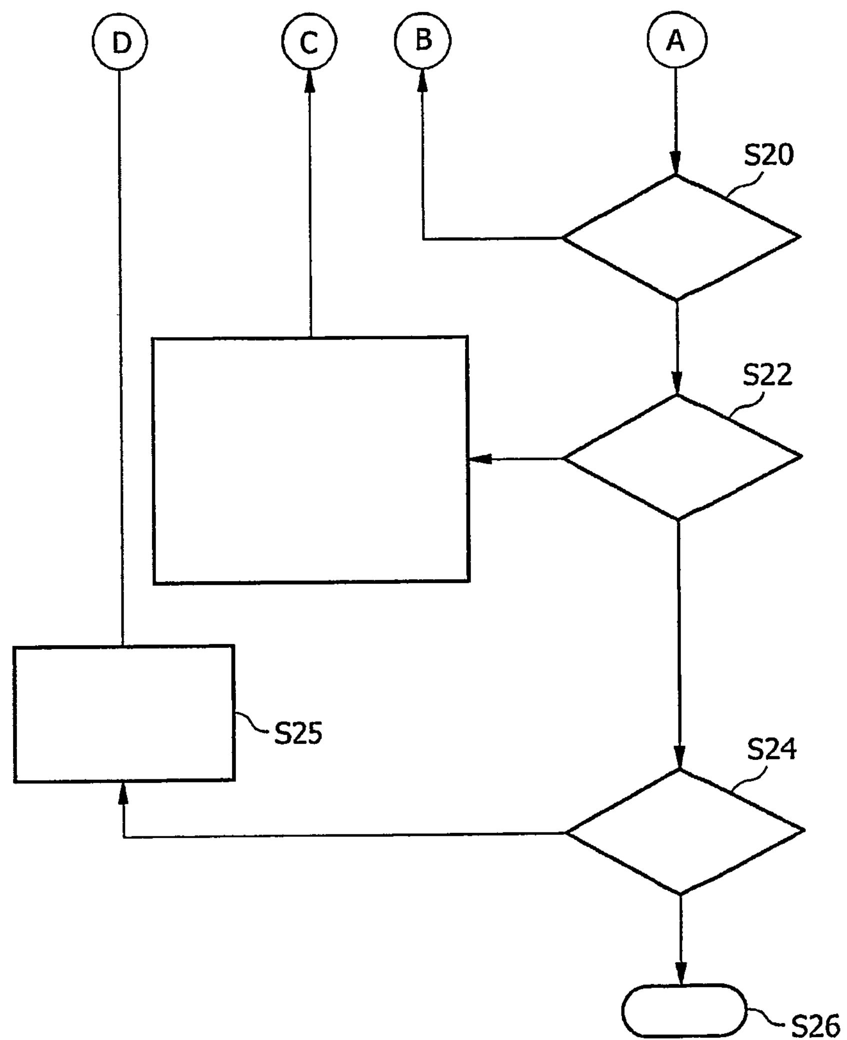

Then, as indicated by the encircled A at the bottom of FIG. 2*a* and at the top of FIG. 2*b*, the method continues to step S20 where it is determined whether there is a distrust entry or not. A user may input a distrust input indicating that in spite of all adjustments made in step S19, no trust has been built up to the diagnosis result i.e. the user does not believe that the diagnosis result is appropriate. In case it is determined in step S20 that there is a distrust entry, as indicated by the encircled B at the top of FIG. 2*b* and at the bottom of FIG. 2*a*, the method continues to step S21 where the first parameter set is adjusted. This may be done by, for example, selecting a different processing method for steps S17 to S19 or by loading another set of first parameters.

According to a variant of this exemplary embodiment of the present invention it may advantageously be possible to automatically forward the diagnostic image data and the corresponding first parameter set which was distrusted by the user to a service port from which it may be downloaded to a R&D department. This data may then be used to further improve the first parameter set to achieve better results.

In case it is determined in step S20 that there is no distrust entry, the method continues to step S22 where it is determined whether there is a trust entry or not. In case it is determined in step S20 that the trust selection option was selected i.e. there was a trust entry, the method continues to step S23 where the diagnostic image data and the first parameter set is added to the comparable data and/or the ground truth and/or is used for adjusting the preset range in step S21. As may be taken from FIG. 2*b* and as indicated by the encircled C at the top of FIG. 2*b* and at the bottom of FIG. 2*a*, the method continues from step S23 to step S21 or to step S13 or to step S12. In a variant, the method may stop at the encircled C, i.e. after step S23.

In case it is determined in step S22 that there was no trust entry, the method continues to step S24 where it is determined whether a learning selection option has been selected i.e. whether there is a learning entry or not. In case it is determined in step S24 that there is a learning entry, the method continues to step S25 where training examples are used to adjust the first parameter set. These training examples may be the diagnostic image data and the corresponding first parameter set added to the memory in step S23 of a previous application run where the result was trusted by the user. Training is possible whenever there are means to determine the true result other than by the data processing method, e.g. by an expert opinion or other diagnostic data acquisitions. As indicated by the encircled D at the top of FIG. 2*b* and at the bottom of FIG. 2*a*, the method continues from step S25 to S15. In a variant, the method may also stop after step S25.

In case it is determined in step S24 that there is not learning entry, the method continues to step S26 where it ends.

Advantageously, as may be taken from the above description, the user may improve the CADx system by him- or herself when there is a corresponding set of ground truth and image data. For example, this set of ground truth and image data may be acquired from an alternative parallel diagnosis. Thus, for example, the user may acquire a ground truth with respect to certain diagnostic image data from an intervention or from another imaging method. Also, an expert opinion may provide for the required ground truth. Then, on the basis of the ground truth, the system may automatically determine a set of parameters which allows for an improved reproduction i.e. for improved diagnosis result. The diagnostic image data and the corresponding ground truth and the thereto belonging parameter set is stored.

Furthermore, as may be taken from above, the system may also be trained which may allow for an automatic selection of appropriate parameters. The system may continuously trained on the basis of training data which is constantly renewed or extended. Thus, by constantly training the system on the basis of a constantly growing set of training data, the system may allow for improved diagnosis result.

For example, the diagnosis may also be performed on the basis of comparable data if, for example, there is no ground truth available. A comparable data set may be determined by, for example, determining a similarity between the current diagnostic image data and image data stored in the memory. Such image similarity may be determined on the basis of global image features. Also, such image similarity may be determined on the basis of statistical properties of image intensities. Also, the method or system may be adapted such that a plurality of comparable images is taken and the most appropriate parameter set and respective variations are determined on the basis of an interpolation between the parameter sets that were valid for all sufficiently similar input images. For the further processing of the diagnostic image data, the parameter set corresponding to the comparable image which has been found may be used subsequently.

Advantageously, in addition to the visualization of confidence intervals, according to the above exemplary embodiment of the present invention, a standardized feedback mechanism is provided which offers similar appearance and user interaction for different embodiments of the invention. Furthermore, advantageously, the confidence intervals are made explorable by user interaction. For example, uncertainty in quantification, registration and segmentation algorithms may be mediated by means of simple sliders. Moving the slider from left to right may result in the presentation of algorithmic results that cover the full confidence range.

FIG. 3 shows an exemplary embodiment of a display that may be displayed on display 4 according to the present invention.

As may be taken from FIG. 3, the display may, for example, be performed in Windows format having a region 30 where the diagnostic image data is displayed. Furthermore, there are provided three button 32, 34 and 36. Button 32 allows for an automatic trust feedback. According to a variant of this exemplary embodiment of the present invention, by activating the trust button 32, the image data currently displayed on area 30 and the corresponding data that may automatically be forwarded to a service port from which it may be distributed for further use. This forwarding may, for example, be performed automatically by email.

The distrust button 34 serves to express the distrust of the user in the segmentation result achieved by means of the current parameter set. Advantageously, by activating the distrust button 34, the diagnostic image data displayed on area 30 and the corresponding parameter set may be forwarded to the service port for further use.

Reference numeral 38 indicates the segmentation result. Line 40 indicates the diagnosis result determined on the basis of the current parameter setting. Dotted lines 42 visualize the confidence intervals. Line 40 represents the diagnostic result when the slider 44 is centered. The user may then explore the confidence interval of the applied algorithm. The segmentation boarder evolves according to the slider position in the confidence range indicated by dotted lines 42. The quantification results change as well from a 95% secured minimal value to a maximal value. Button 36 "train known standard" may allow the user to manually correct the contour. According to a manual correction of the contour, the system may then adjust parameters of the segmentation accordingly.

The "train known standard" button 36 may be used to adjust technical parameters that influence the algorithms performance. Whenever a second opinion, for example an expert's subjective visual impression or a ground truth measurement is available, these results can be trained into the algorithm. Using the "learning from examples" paradigm as, for example, described in Bredno J. et. al.: "Automatic Parameter Setting For Balloon Models" Procs. SPIE 3979, pp 1185-1195, 2000 which is hereby incorporated by reference, technical parameters are adjusted so that the ground truth is reproduced by the algorithm. According to a variant of this exemplary embodiment, this learning from examples may further include a regression analysis that is able to adjust technical parameters based on global input's data characteristics, such as described in Lehmann T. M. et. al.: "Texture-Adaptive Active Contour Models" LNCS 2013, pp 387-396, 2001 which is hereby incorporated by reference.

Advantageously, according to the present invention, a multi-step method is provided which is applicable to a variety of image- and signal processing methods that are the base of clinical applications and which are applied to computer-aided diagnosis. Results of such algorithms include quantitative measurements, transformation parameters for registration, geometric segmentation results or others. According to the present invention, the trust of users towards such systems and the diagnosis results may be improved.

It should be noted that the present application is not limited to the field of computer-aided diagnosis but may also be applied to similar fields like intervention planning, navigation support and outcome control where quantitative information is extracted from medical data acquisitions.

The invention claimed is:

1. A method of computer-aided extraction of quantitative information, the method comprising the steps of:

acquiring primary data from an object to be examined;

processing the primary data on the basis of a primary parameter set to determine a primary result;

determining a confidence interval with respect to the primary result;

displaying the primary result and the confidence interval, wherein the displaying includes an image of the object including a visualization of the primary result and the confidence interval;

adjusting the primary parameter set on the basis of a user input, the adjusting being within a predetermined range;

reprocessing the primary data on the basis of the adjusted primary parameter set to determine a secondary result;

displaying the secondary result;

providing a distrust selection option to a user;

forwarding the primary data and the primary parameter set to a service port when the distrust selection option is selected by the user.

2. The method of claim 1, wherein the primary parameter set comprises a plurality of parameters; varying at least one parameter of the primary parameter set; adjusting the primary parameter set on the basis of the at least one parameter which is varied; and interactively reprocessing the primary data on the basis of the adjusted parameter set to determine the secondary result and displaying the secondary result.

3. The method of claim 1, further comprising the steps of:

providing a trust selection option to a user; and storing the primary parameter set in correspondence with the primary data when the trust selection option is selected by the user.

4. The method of claim 1, further comprising the steps of:

comparing the primary diagnostic data to secondary data;

deciding whether the primary data is comparable to any of the secondary data;

reprocessing the primary data on the basis of a secondary parameter set belonging to similar secondary data to determine a tertiary result; and displaying the tertiary result.

5. The method of claim 1, wherein the method allows for an explorative determination of a dependability of at least one of the primary and secondary results.

6. Data processing device, comprising:

a memory for storing primary data from an object to be examined and a primary parameter set;

a processor for processing the primary data for a computer-aided extraction of quantitative information to determine a primary and a secondary result; and a display for displaying the primary and secondary results;

wherein the primary data is processed by the processor on the basis of a primary parameter set to determine a primary result;

wherein a confidence interval is determined by the processor with respect to the primary result;

wherein the primary result and the confidence interval are displayed on the display, wherein the displaying includes an image of the object including a visualization of the primary result and the confidence interval;

wherein the primary parameter set is adjusted on the basis of an input by the processor, the adjustment being within a predetermined range;

wherein a reprocessing the primary data on the basis of the adjusted primary parameter set to determine a secondary result is performed by the processor, wherein the secondary result is displayed on the display wherein a distrust selection option is provided to a user on the display; and wherein the processor forwards the primary data and the primary parameter set to a service port when the distrust selection option is selected by the user.

7. Computer program embodied on a non-transitory computer readable medium for a data processing device for performing a computer-aided extraction of quantitative information, wherein, when the computer program is executed on a data processor of the data processing device, the data processing device executes the following steps:

acquiring primary data from an object to be examined;

processing the primary data on the basis of a primary parameter set to determine a primary result;

determining a confidence interval with respect to the primary result;

displaying the primary result and the confidence interval, wherein the displaying includes an image of the object including a visualization of the primary result and the confidence interval;

adjusting the primary parameter set on the basis of a user input the adjusting being within a predetermined range;

reprocessing the primary data on the basis of the adjusted primary parameter set to determine a secondary result;

displaying the secondary result providing a trust selection option to a user; and storing the primary parameter set in correspondence with the primary data when the trust selection option is selected by the user.

8. The method of claim 6, further comprising the steps of:

providing a trust selection option to a user; and storing the primary parameter set in correspondence with the primary data when the trust selection option is selected by the user.

9. The method of claim 7, further comprising the steps of:

providing a distrust selection option to a user; and forwarding the primary data and the primary parameter set to a service port when the distrust selection option is selected by the user.

* * * * *